United States Patent
Deevi et al.

(10) Patent No.: US 7,538,324 B2
(45) Date of Patent: May 26, 2009

(54) DETECTION OF NITRATES FROM TOBACCO FOR CORRELATION WITH THE AMOUNT OF TOBACCO-SPECIFIC NITROSAMINES WITHIN THE TOBACCO

(75) Inventors: Seetharama C. Deevi, Midlothian, VA (US); Edward L. Carmines, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 11/902,347

(22) Filed: Sep. 20, 2007

(65) Prior Publication Data

US 2008/0094625 A1   Apr. 24, 2008

Related U.S. Application Data

(60) Provisional application No. 60/846,107, filed on Sep. 21, 2006.

(51) Int. Cl.
*G01N 21/17*   (2006.01)
(52) U.S. Cl. .............................. 250/339.11
(58) Field of Classification Search ............. 250/339.11
See application file for complete search history.

(56) References Cited

U.S. PATENT DOCUMENTS

| 4,082,950 A | 4/1978 | Chen |
| 4,566,469 A | 1/1986 | Semp et al. |
| 4,888,484 A | 12/1989 | Harvey |
| 5,476,108 A | 12/1995 | Dominguez et al. |
| 5,810,020 A | 9/1998 | Northway et al. |

FOREIGN PATENT DOCUMENTS

| EP | 1199555 A | 4/2002 |
| WO | WO2005/111583 A | 11/2005 |

OTHER PUBLICATIONS

Analytical Spectral Devices, Inc., Using NIR Reflections to Analyze Menthol Concentration in Tobacco, M1003—Menthol Concentration in Tobacco, Copyright © by Analytical Spectral Devices, Inc. 2004.

NTech Industries, Inc., Model 505 GreenSeeker Hand Held™ Optical Sensor Unit, Operating Manual, GreenSeeker, 500-1-030, pp. 1-18, Rev. G: Apr. 28, 2005.

Precision Agriculture, Sensors for Information Gathering, Developed by: Prof. Shrini Upadhyaya and Adunias Teixeira, pp. 1-22, Sep. 22, 2006, http://www.precisionag.org/html/ch10.html.

(Continued)

*Primary Examiner*—Constantine Hannaher
(74) *Attorney, Agent, or Firm*—Buchanan Ingersoll & Rooney PC

(57) ABSTRACT

A system for detecting nitrates in a tobacco sample having a light source, and a detection device. The light source provides a beam of light incident to a tobacco sample, which is reflected from the tobacco sample to the detection device. A computing device computes the amount of nitrates within the tobacco sample based on data received from the detection device to correlate the amount of tobacco-specific nitrosamines within the tobacco sample.

18 Claims, 6 Drawing Sheets

OTHER PUBLICATIONS

Li, Folin et al., "Detection of Nitrogen Status in FCV Tobacco Leaves with the Spectral Reflectance", Geoscience and Remote Sensing Symposium, 2005, IGARSS '05. Proceedings. 2005 IEEE International Seoul, Korea Jul. 25-29, 2005, Piscataway, NJ, USA, IEEE, Jul. 25, 2005, pp. 1863-1866, XP010849176 ISBN: 0-7803-9050-4.

Verma, Santosh Kumar et al., Nondestructive and rapid determination of nitrate in soil, dry deposits and aerosol samples using KBr-matrix with diffuse reflectance Fourier transform infrared spectroscopy (DRIFTS), Analytica Chimica ACTA, Elsevier, Amsterdam, NL, vol. 582, No. 2, Sep. 16, 2006, pp. 382-389, XP022209424 ISSN: 0003-2670.

Anonymous, "FieldSpec HandHeld Pro Portable Spectroradiometer for Field Applications Industries", Internet article, Feb. 12, 2006, XP002475943.

Fischer, Sophia et al., Performed tobacco-specific nitrosamines in tobacco-role of nitrate and influence of tobacco type, Carcinogenesis, IRL Press, London, GB, vol. 10, No. 8, 1989, pp. 1511-1517, XP003008119 ISSN: 0143-3334.

International Search Report and Written Opinion dated Jun. 3, 2008 for PCT/IB2007/003722 not a publication.

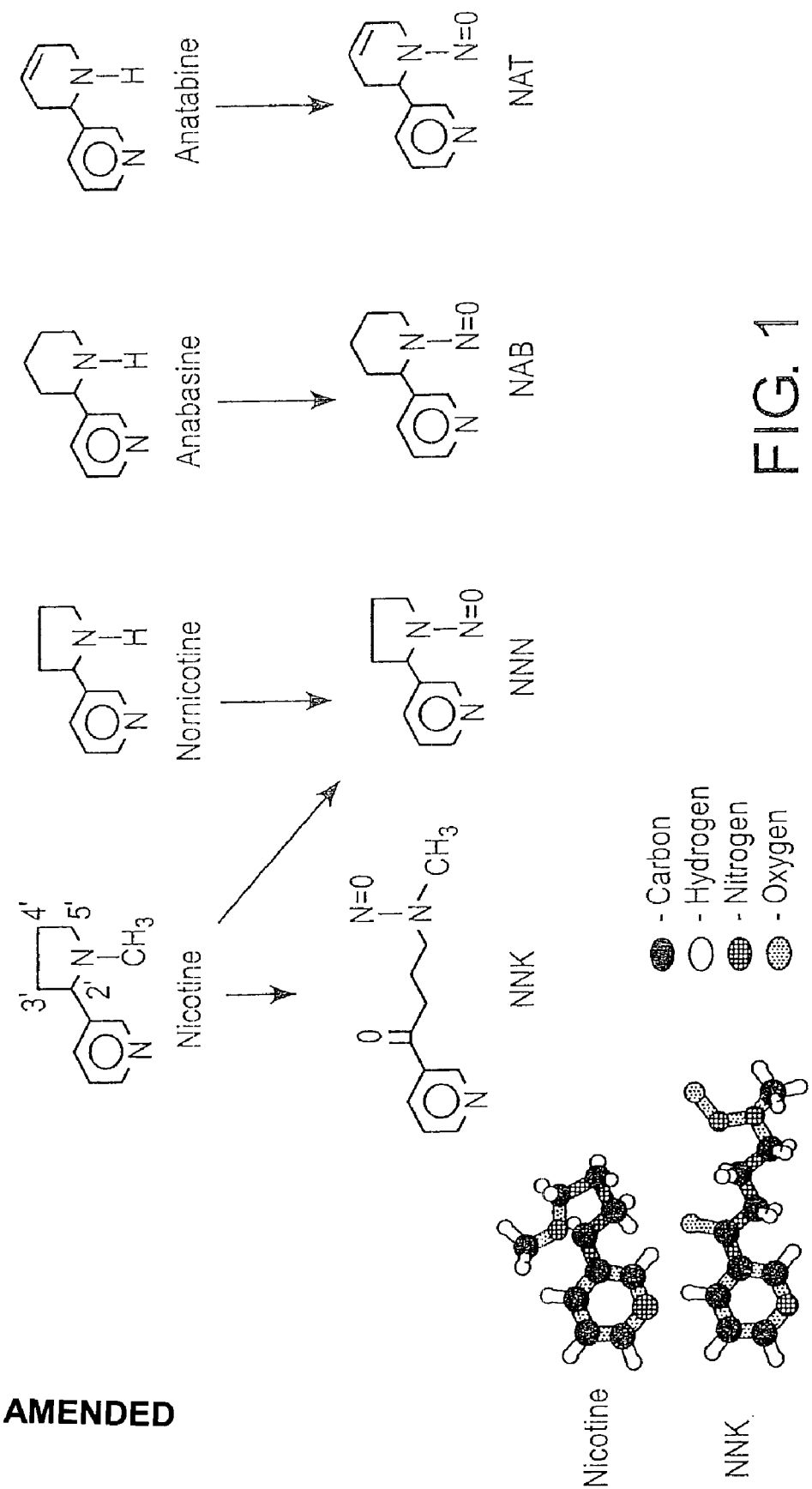
FIG. 1
AMENDED

DETECTION OF NITRATES FROM TOBACCO FOR CORRELATION WITH THE AMOUNT OF TOBACCO-SPECIFIC NITROSAMINES WITHIN THE TOBACCO

CROSS REFERENCE TO RELATED APPLICATION

This application claims priority under 35 U.S.C. §119(e) to U.S. provisional Application No. 60/846,107, filed on Sep. 21, 2006, the entire content of which is incorporated herein by reference.

SUMMARY

In accordance with one embodiment, a system for detecting nitrates in a tobacco sample comprises: a light source, wherein the light source provides a beam of light incident to a tobacco sample; a detection device that detects light from the light source reflected from the tobacco sample; and a computing device that computes the amount of nitrates within the tobacco sample based on data received from the detection device.

In accordance with a further embodiment, a method of detecting nitrates within a tobacco sample comprises: exposing a tobacco sample to an incident beam from a light source; detecting the incident beam reflecting from the tobacco sample at one or more wavelengths; and computing an amount of nitrates within the tobacco sample by comparing data from the at least one wavelength to an index of nitrates within the tobacco sample.

BRIEF DESCRIPTION OF THE DRAWINGS

FIG. 1 shows a series of chemical drawings showing tobacco-specific nitrosamines (TSNAs) in $CH_3CN$ stock solution.

DETAILED DESCRIPTION

Figure 2:
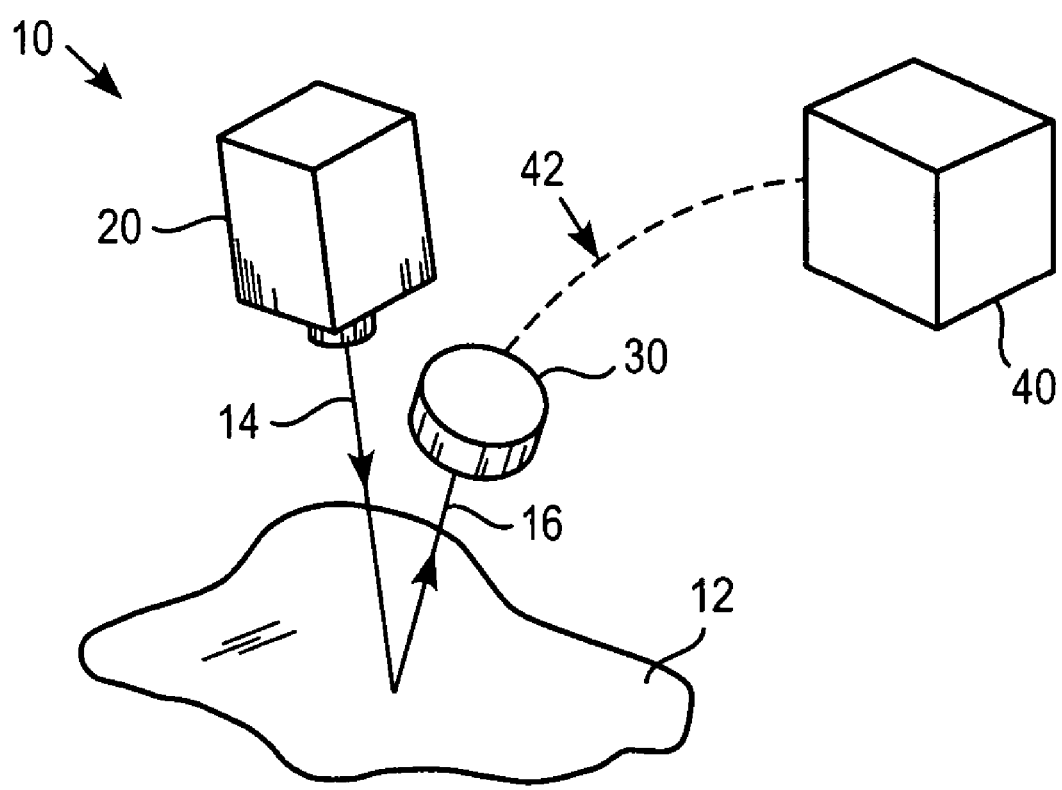
FIG. 2 shows a schematic illustration of a spectroscopy arrangement for a system for detecting nitrates from tobacco leaves or tobacco samples according to one embodiment.

Tobacco and tobacco products contain a number of nitrogen-containing substances, which during burning of the tobacco, can yield various components in the smoke, such as nitric oxide, nitrogen dioxide, methyl nitrate and tobacco-specific nitrosamines (TSNAs). Accordingly, it would be desirable to be able to detect the amount of nitrates within a tobacco sample, which can be then be correlated with the amount of tobacco-specific nitrosamines (TSNAs) for smokeable and non-smokeable products.

Tobacco-specific nitrosamines (TSNAs) are structurally similar to the nicotine compounds from which they are typically derived. As shown in FIG. 1, nitrosamines are chemical compounds of the chemical structure ($R_2$—N—N=O), which are typically produced from nitrites ($NO_2$) and amines ($R_2NH$) under certain conditions, including strong acidic conditions. Tobacco-specific nitrosamines (TSNAs) can be formed during tobacco curing by nitrosation of the tobacco alkaloids. NNN (N'-Nitrosoamine), NAB (N'-Nitrosoanabasine), NAT (N'-Nitrosoanatabine) and NNK (4-(Methylnitrosamino)-1-(3-pyridyl)-1-butanone) are formed predominantly by N-nitrosation of the corresponding secondary amine. NNK can be formed from nicotine by oxidation N-nitrosation following ring openings of the pyrrolidine ring.

Current analytical techniques of measuring nitrates and/or tobacco-specific nitrosamines (TSNAs) require extensive laboratory equipment, which is not typically found in the tobacco growing and curing environment. Samples such as tobacco are ground, extracted with methylene chloride or alkaline aqueous solutions, and subjected to extensive differential extraction. The final sample is then analyzed by gas chromatography using a thermal energy analyzer for detection (GC-TEA). Other currently available instruments to measure tobacco-specific nitrosamines (TSNAs) include gas chromatography (GC), high performance liquid chromatography (HPLC), gas chromatography/mass spectroscopy (GC/MS), thermal energy analyzer (TEA), or combinations thereof. Although, these methods provide accurate identification, quantification, low detection limits, and high selectivity and sensitivity, these methods also require sophisticated analytical devices and extensive processing of tobacco. In addition, these currently accepted methods are expensive and time consuming, with a single analyst typically having the capacity to process only 20 samples per eight hour shift. While robotic sample preparation methods exist, the cost is prohibitive.

In addition, tobacco-specific nitrosamine (TSNA) sample preparation generates vast quantities of waste solvent, the disposal of which is also costly. Therefore, a method and/or system for the detection of nitrates, which can be correlated to tobacco-specific nitrosamines (TSNAs) in tobacco products and/or leaves, which is inexpensive, fast and easy to perform would be desirable. In addition, since current measurement procedures for sensing and identifying tobacco-specific nitrosamines (TSNAs) are both complicated and costly, it would be desirable to have a hand-held device, which is rugged, portable, lightweight, (i.e., preferably less than 1 kg), and simple to use.

In accordance with one embodiment, a system for detecting nitrates from tobacco leaves includes a light source, wherein the light source provides a beam of light incident to a tobacco sample, a detection device that detects light from the light source; and a computing device that computes the amount of nitrates within the tobacco sample based on data received from the detection device. The light source is preferably a laser type device that produces infrared (IR) or near infrared (NIR) light having a wavelength of approximately 750 nm to approximately 2,500 nm. It can be appreciated that any suitable spectroscopic technique can be used to identify nitrates and to investigate the composition of a tobacco sample. In addition, the system preferably includes an infrared or near infrared spectroscopy correlation table to correlate the spectroscopy findings with the data received from the tobacco sample.

In accordance with one embodiment, the use of infrared spectroscopy can be used for the detection of nitrates within a tobacco sample. Infrared spectroscopy is based on the principle that the chemical bonds of specific compounds have specific frequencies at which they vibrate corresponding to energy levels. The resonant frequencies or vibrational frequencies are determined by the shape of the molecular potential energy surfaces, the masses of the atoms and, eventually by the associated vibronic coupling. A simple diatomic molecule has only one bond, which may stretch, while more complex molecules may have many bonds, and vibrations can be conjugated, leading to infrared absorptions at characteristic frequencies that can be related to the detection of nitrates and correlated to tobacco-specific nitrosamines within a tobacco sample.

In order to measure a sample, a beam of infrared light is passed through the sample, and the amount of energy absorbed at a single wavelength or at a plurality of wavelengths is recorded. From this, a transmittance or absorbance spectrum may be plotted, which shows at which wavelengths the sample absorbs the infrared (IR) or near infrared (NIR) light, and allows an interpretation of which bonds are present. This technique works almost exclusively on covalent bonds, and as such is of most use in organic chemistry. Clear spectra can be obtained from samples with few infrared (IR) or near infrared (NIR) active bonds and high levels of purity. More complex molecular structures lead to more absorption bands and more complex spectra.

In accordance with an embodiment, the detection of nitrates from tobacco leaves (to correlate tobacco-specific nitrosamines (TSNAs) from tobacco leaves) for applications in smokeable and non-smokeable products can be based on an infrared (IR) or near-infrared (NIR) detection of the amount of nitrate ($NO_3$) including the nitrogen-oxygen bond in the tobacco leaves or tobacco sample. The tobacco leaves or tobacco samples can be leaves on the plant before harvesting, ripened leaves, which have been removed from the plant, and/or dried or cured tobacco leaves at any stage of the curing process or in the form of tobacco cut filler. The data received from the infrared (IR) or near-infrared (NIR) detection from the tobacco sample or tobacco leaves is then correlated to a reference table or index using a suitable method or technique to correlate the amount of nitrates within the tobacco sample to tobacco-specific nitrosamines (TSNAs)

FIG. 2 shows a system 10 for detecting nitrates and correlating the amount of nitrates within a tobacco leaf or tobacco sample 12 to an amount of tobacco-specific nitrosamines within the tobacco leaf or tobacco sample 12, wherein the sample 12 can be unprocessed or processed tobacco. The system 10 comprises a light source 20, a detection device 30 and a computing device 40 that computes the amount of nitrates within a tobacco sample based on data received from the detection device 30. The light source 20 and the detection device 30 are preferably contained within a housing or casing 110 (FIG. 4), however, it can be appreciated that the light source 20 and the detection system 30 can be contained within a sensor or probe-like device 150 (FIG. 5), which can be connected to the system 10 via a cable 42.

The computing device 40 can be included within the housing of the system 10 or can be attached via a suitable connection 42, which can be a fixed or hard wire, or via the emission of a wireless signal to a remote computing device 40. The system 10 is preferably designed to be used by field personnel to check the amount of nitrates present in growing or harvested tobacco leaves, wherein a determination can be made regarding use of fertilizer or whether to accept or reject the crop or portion thereof based on the amount of nitrates within the tobacco leaves or tobacco sample.

The light source 20 preferably produces infrared (IR) or near-infrared (NIR) light of multiple wavelengths in an extended short wave region of interest such as from about 550 to about 2,500 nanometers (nm). However, it can be appreciated that any suitable light source can be used, which produces a beam of light having a wavelength between about 300 nm and 2,700 nm. In addition, the light source 20 can be a tunable or quasi-monochromatic light source in the form of a laser, wherein the light source provides a beam of light incident to the tobacco sample, over multiple, distinct wavelengths and is incident upon the tobacco sample whose reflectivity or reflectance index is known. In use, the light source 20 produces a beam of light and by measuring the incident and reflected light intensity, and based on the intensity of the reflected light, the material reflectivity can be determined.

The detection device 30 is preferably a photodiode sensor, on optical detector or other suitable sensor for the detection of the light source upon reflection from the tobacco leaf and/or tobacco sample 12. In use the light source 20 is tuned to at least one wavelength, wherein a portion of the light 14 is reflected upon the tobacco sample 12, and a portion of the light 16 is detected by the detection device 30. It can also be appreciated that the wavelength of the light source 20 can be varied, such that the light source 20 can be adapted or tunable to produce at least two wavelengths with the reflectivity or reflectance measured at each wavelength. In accordance with one embodiment, the wavelength of light can be varied in increments of 0.1 nm to 20 nm and more preferably 1 to 10 nm. The resulting reflectivity or reflectance is then used to determine the amount of nitrates within the tobacco leaves or sample 12.

In accordance with one embodiment, the system 10 can include a computing device 40 (e.g. computer or microprocessor), that computes the amount of nitrates within the tobacco sample 12 based on data received from the detection device 30. The computing device 40 preferably holds stored reference data and the recorded spectra or data are compared to the stored reference data to simply compute a direct value for the particular analysis being carried out. In addition, upon request the system 10 can display the data or results in a desired format. It can be appreciated that based on the received information, the computing device can identify the amount of nitrates within the tobacco sample or tobacco leaf 12, which can be used to compute the amount of tobacco-specific nitrosamines (TSNAs) within the tobacco leaf or tobacco sample 12. The computing device 40 can be connected 42 to the detection device 30 via a hard wire or a wireless connection.

Figure 3:
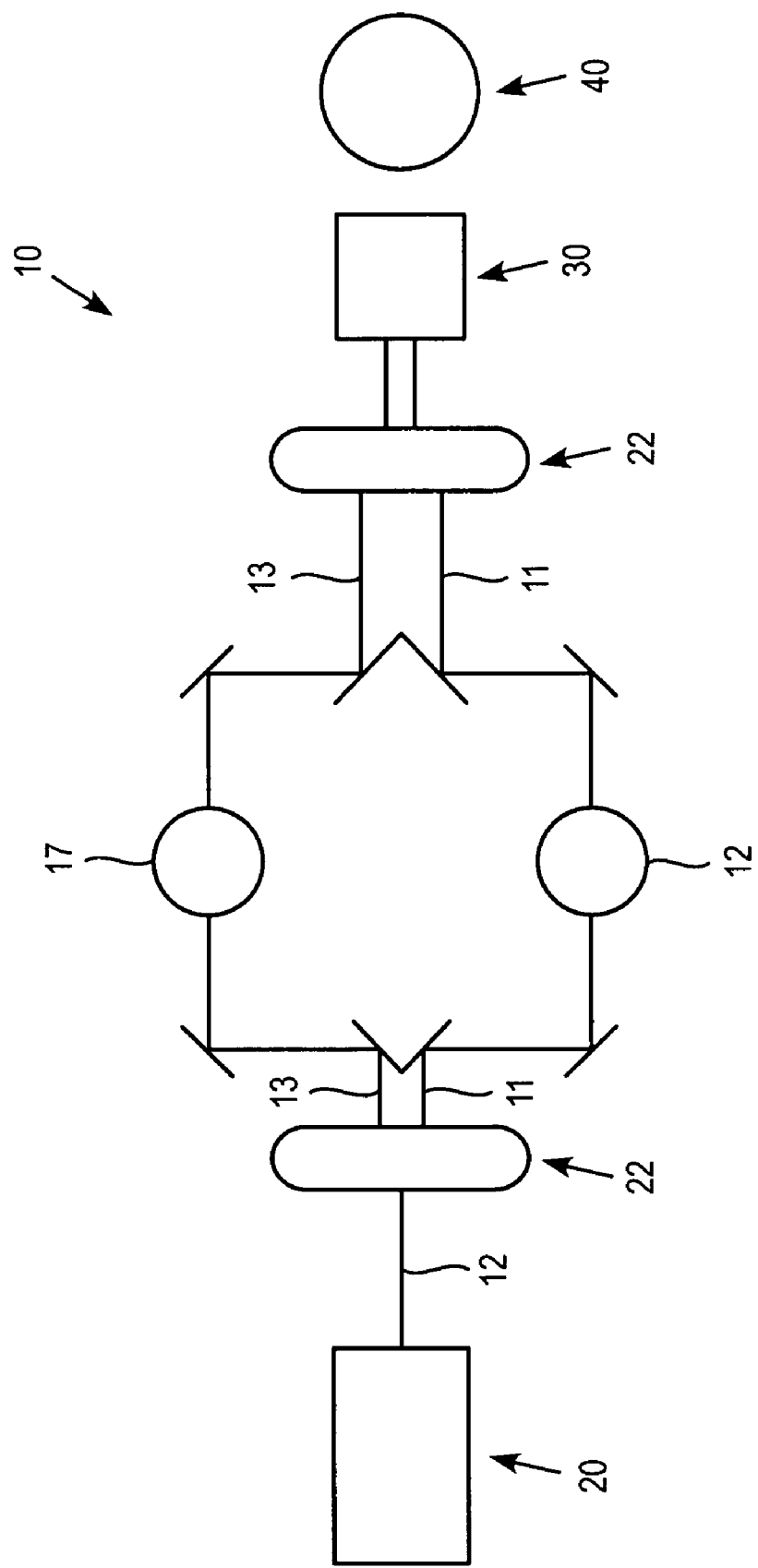
FIG. 3 shows a schematic illustration of a spectroscopy arrangement for a system for detecting nitrates in according with a further embodiment.

FIG. 3 shows a system 10 for detecting nitrates in accordance with another embodiment. The system 10 includes a light source 20, beam splitters 22, a reference sample and a tobacco sample, a detection device 30 and a computing device 40. As shown in FIG. 3, the light source 20 produces a beam of infra-red light or near infra-red light 12, which enters the beam splitter 22 wherein the beam splitter 22 splits the beam of light from the light source into a measurement light path 11 and a reference light path 13, and wherein the measurement light path or beam 11 is directed to the tobacco sample 12, and wherein the reference light path or beam 13 is directed to a reference material 17, which is used to calibrate the light wavelength. The beams 11, 13 are both reflected back towards a detection device 30, however typically the beams 11, 13, first pass through a beam splitter 22 which alternates which of the two beams 11, 13 enters the detection device 30. A computing device 40 receives reference data from the detection device 30, which is stored and processed into a printout or digital readout of the amount of nitrates, and more preferably the amount of tobacco-specific nitrosamines (TSNAs) within the tobacco sample 12.

Figure 4:
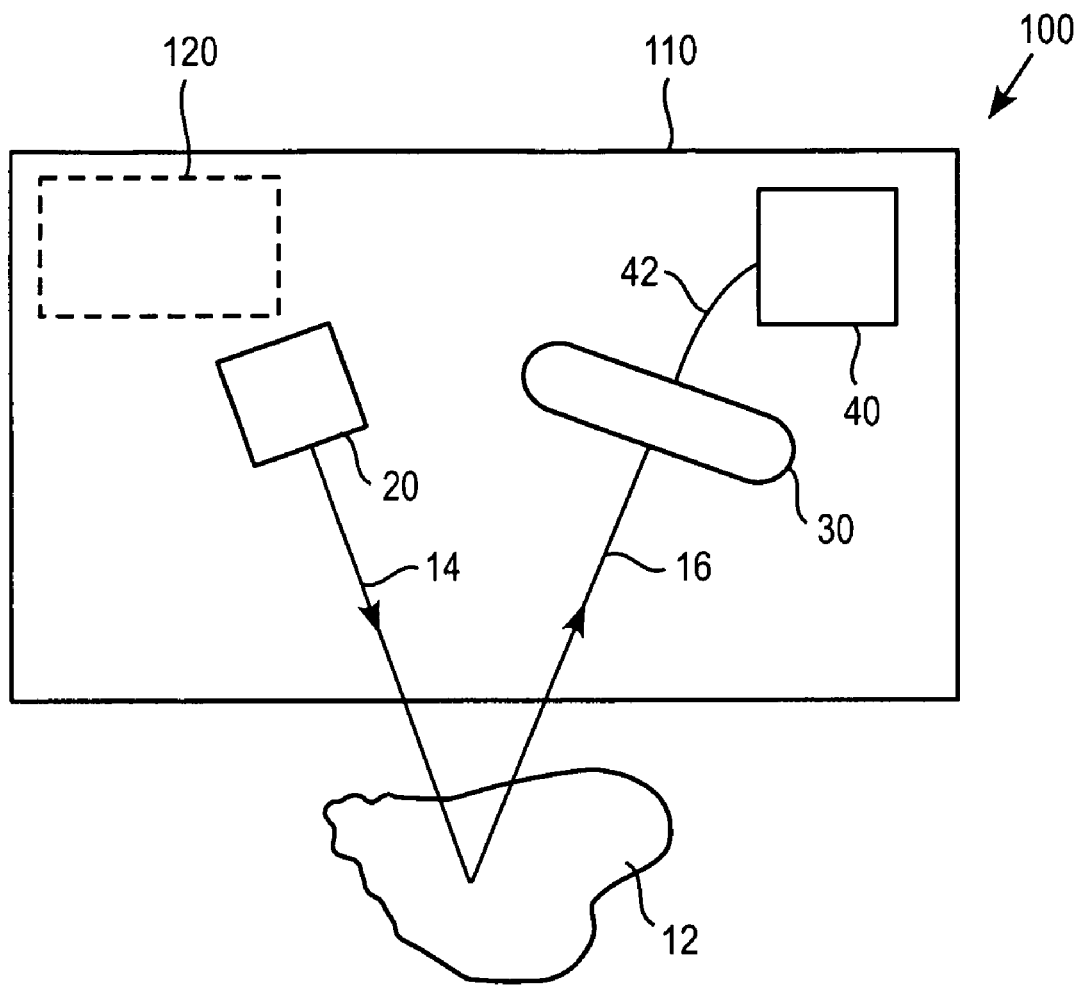
FIG. 4 shows a schematic illustration of a spectroscopy arrangement for a system for detecting nitrates from tobacco leaves or tobacco samples according to another embodiment.

FIG. 4 shows a schematic diagram of a handheld system 100 for the detection of nitrates from tobacco leaves or tobacco samples 12, which can be used to correlate the amount of tobacco-specific nitrosamines within tobacco leaves or tobacco sample 12. As shown in FIG. 4, the handheld system 100 for the detection of nitrates from tobacco leaves or sample 12 includes a housing or casing 110, which preferably contains a light source 20, a detection device 30 and a computing device 40, that computes the amount of nitrates within a tobacco sample 12 based on data received from the detection device 30. It can be appreciated that the system 100 can also include beam splitter (not shown), wherein the beam splitter splits the beam of light from the light source 20 into a measurement light path and a reference light path. In use, the measurement light path is directed to the tobacco leaf or tobacco sample 12, with the reference light path used to calibrate the wavelength of the beam of light.

The housing or casing 110 can include an electronic screen or display 120 for displaying the data or results in a desired format. The handheld system 100 is preferably constructed from a suitable material, including plastics, synthetic or semi-synthetic polymerization products. The system 100 is preferably portable and should be able to withstand use in a field environment. The system 100 also preferably has a total weight of less than 5 kilograms and more preferably less than 1.0 kilograms. The system 100 also preferably provides a reading within approximately 10 seconds of obtaining the data from the tobacco leaf or tobacco sample 12. However, it can be appreciated that the data can be stored within the computing device 40 and subsequently downloaded to a second computing device (not shown), wherein additional computations or analysis can be performed.

Figure 5:
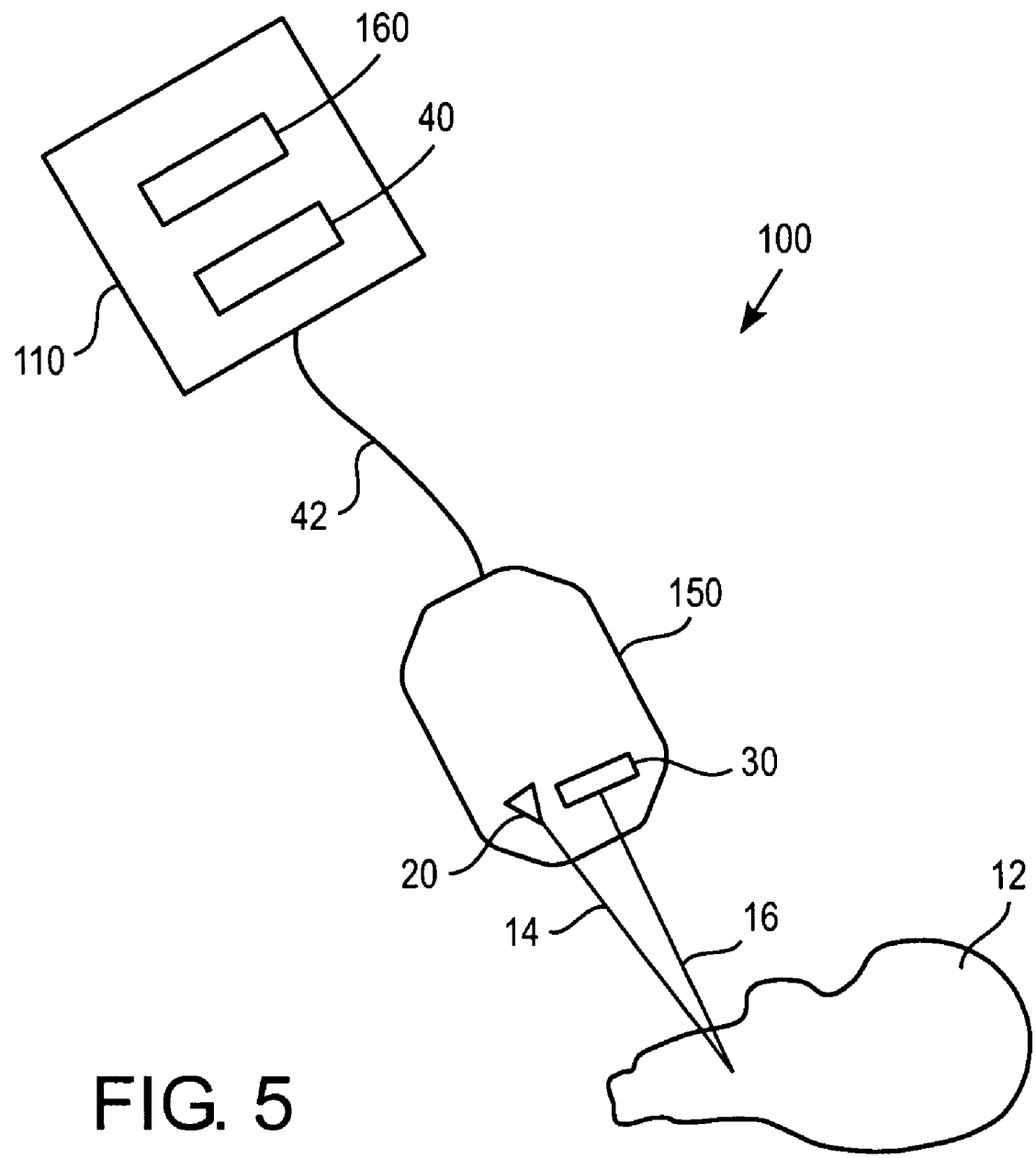
FIG. 5 shows a schematic illustration of a spectroscopy arrangement for a system for detecting nitrates from tobacco leaves or tobacco samples according to a further embodiment.

FIG. 5 shows a schematic illustration of a spectroscopy arrangement for a system 100 having a sensor device 150 for detecting nitrates from tobacco leaves or tobacco samples 12 according to another embodiment. As shown in FIG. 5, the sensor or sensing device 150 can include the light source 20 and the detection device 30. The system 100 also includes a housing or casing 110, which preferably contains the computing device 40 and any additional electronic components 160 including a power source. The power source is preferably a rechargeable power source or battery, which can be used in a tobacco field without an electrical power source. Alternatively, the light source 20 and the detection device 30 can be contained within the housing 110, wherein the sensor or sensing device 150 can be attached to the housing 110 via a suitable connection 42, such as an optical cable, and wherein the sensor or sensing device 150 includes a suitable optical probe.

In accordance with one embodiment, a handheld system 100 to identify and monitor nitrates within a tobacco sample can comprise an infrared (IR) or near-infrared (NIR) sensor based system, which calculates the amounts of nitrates by measuring the nitrogen-oxygen bond. The system 100 preferably uses a non-destructive analysis method that produces a measurement or test result in less than about 10 seconds, and requires none or only minimal processing of the tobacco or tobacco product with an error range of less than about 10 percent. In addition, it can be appreciated that the system 100 will preferably have a quantitative ability to provide a detection range for nitrates of about 1,000 to 30,000 ppm (parts-per-billion), and more preferably a detection range of about 1,000 to 5,000 ppm. The system 100 also is preferably operable over a temperature range of about 0 to 40 degrees Celsius.

Figure 6:
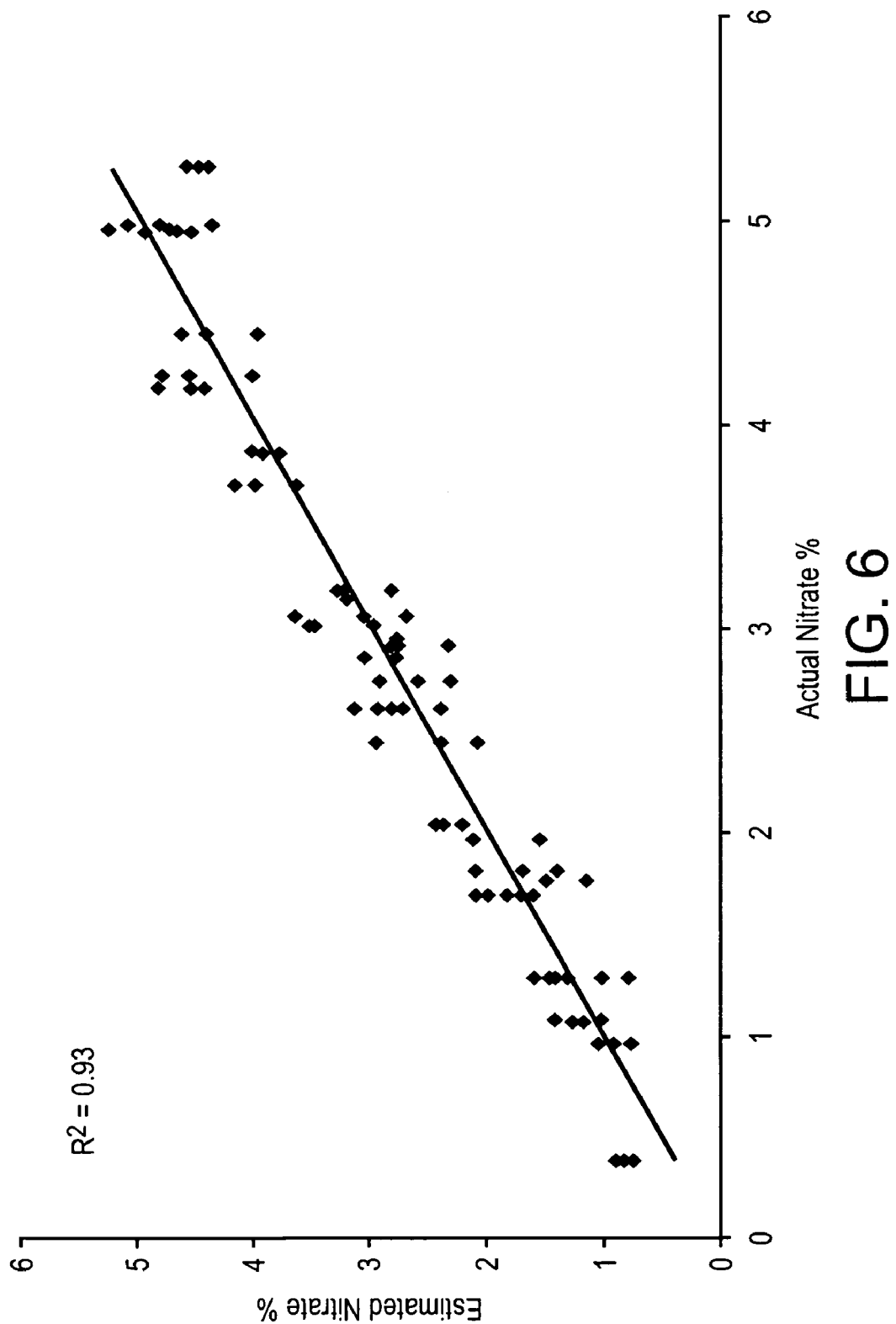
FIG. 6 is a graph showing exemplary estimated nitrate levels of Burley tobacco samples as compared to exemplary actual nitrate levels of each Burley tobacco sample.

FIG. 6 is a graph showing cross-validated test data between actual nitrate levels and estimated nitrate levels obtained by near infrared spectroscopy of tobacco leaves using ASD Lab-Spec 2500 (Available from Advanced Spectral Devices, Inc. of Boulder, Colo.) with a High Intensity Contact Probe and processing to estimate nitrate levels. The graph shows estimated nitrate content (vertical axis) as compared to actual nitrate levels (horizontal axis) for each sample of Burley tobacco as can be determined using standard chemical analysis.

Preferably, the estimated nitrate level of each Burley tobacco sample using the nitrate detection system is within about ±30% of the actual nitrate levels, and more preferably within about ±20%.

It will be understood that the foregoing description is of the preferred embodiments, and is, therefore, merely representative of the article and methods of manufacturing the same. It can be appreciated that variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. A system for detecting nitrates in a tobacco sample comprising:
    a light source, wherein the light source provides a beam of light incident to a tobacco sample;
    a detection device that detects light from the light source reflected from the tobacco sample, and
    a computing device that computes the amount of nitrates within the tobacco sample based on data received from the detection device and a tobacco-specific nitrosamine content of the tobacco sample based on the amount of nitrates computed to be within the tobacco sample.

2. The system of claim 1, wherein the detection device detects the amount of nitrates based on the amount of energy absorbed at a single wavelength or at a plurality of wavelengths thereby indicating the presence of nitrogen oxygen bonds within nitrates.

3. The system of claim 1, wherein the light source is an infrared light source having a wavelength of between about 300 nm and 1200 nm.

4. The system of claim 1, wherein the light source is a near-infrared light source having a wavelength of between about 1200 nm and 2700 nm.

5. The system of claim 1, wherein the light source is a laser, a tunable light source and/or a quasi-monochromatic light source.

6. The system of claim 1, wherein the light source produces infrared and/or near infrared light having a wavelength of about 300 to about 2500 nanometers (nm).

7. The system of claim 1, wherein the detection device is a photodiode sensor or an optical sensor.

8. The system of claim 1, further comprising a beam splitter, wherein the beam splitter splits the beam of light from the light source into a measurement light path and a reference light path, and wherein the measurement light path is directed to the tobacco sample, and wherein the reference light path is used to calibrate light wavelength.

9. The system of claim 1, wherein the light source and the detection device are contained within a sensor.

10. The system of claim 9, wherein the computing device is contained within a housing, and wherein the housing and a probe are connected to one another via a cable.

11. The system of claim 1, wherein the sample is ground tobacco in a liquid medium.

12. A method of detecting nitrates within a tobacco sample comprising:
    exposing a tobacco sample to an incident beam from a light source;

detecting the incident beam reflecting from the tobacco sample at one or more wavelengths;

computing an amount of nitrates within the tobacco sample by comparing data from the one or more wavelengths within the tobacco sample to an index of amount of nitrates present in a reference log;

determining the amount of tobacco-specific nitrosamines within the tobacco sample based on the amount of nitrates computed to be within the tobacco sample.

13. The method of claim 12, further comprising exposing the tobacco sample to at least two different wavelengths.

14. The method of claim 12, wherein the light source is an infrared light source and/or a near-infrared light source.

15. The method of claim 12, wherein the light source is a laser, tunable light source, and/or quasi-monochromatic light source.

16. The method of claim 12, wherein the light source produces infrared or near infrared light having a wavelength of about 300 to about 2500 nanometers (nm).

17. The method of claim 12, wherein detecting the incident beam reflecting from the tobacco sample at one or more wavelengths is performed with a photodiode sensor and/or an optical sensor.

18. The method of claim 12, wherein the sample is ground tobacco in a liquid medium.

* * * * *